United States Patent [19]

Akiyama

[11] 3,948,271
[45] Apr. 6, 1976

[54] DRAIN FOR THE EARDRUM AND APPARATUS FOR INTRODUCING THE SAME

[76] Inventor: Taichiro Akiyama, 19-23, Shimoochiai 2-chome, Shinjuku, Tokyo, Japan

[22] Filed: Jan. 27, 1975

[21] Appl. No.: 544,347

Related U.S. Application Data

[62] Division of Ser. No. 410,688, Oct. 29, 1973, Pat. No. 3,888,258.

[30] Foreign Application Priority Data
Nov. 7, 1972 Japan............................. 47-111376
Nov. 7, 1972 Japan............................. 47-128293

[52] U.S. Cl. ........................ 128/350 R; 128/334 R
[51] Int. Cl.² .................................... A61M 27/00
[58] Field of Search ................... 128/334 R, 350 R

[56] References Cited
UNITED STATES PATENTS

| | | | |
|---|---|---|---|
| 2,127,903 | 8/1938 | Bowen | 128/334 R |
| 3,530,860 | 9/1970 | Majoros | 128/350 R X |
| 3,563,925 | 2/1971 | Kliment et al. | 128/334 R X |
| 3,818,894 | 6/1974 | Wichterle et al. | 128/334 R X |
| 3,862,452 | 1/1975 | Wichterle et al. | 3/1 |

FOREIGN PATENTS OR APPLICATIONS
123,660    4/1959    U.S.S.R........................... 128/334 R

*Primary Examiner*—Channing L. Pace
*Attorney, Agent, or Firm*—McDougall, Hersh & Scott

[57] ABSTRACT

A drain for the eardrum is formed of a high polymer with the properties of absorbency and swelling. An apparatus for inserting the drain for the eardrum includes a needle with a sharp tip, a tube sheathing the needle and a trigger to project the sharp end of the needle from the end of the tube. When the trigger is drawn, the sharp tip of the needle is extended from the end of the tube and is then inserted into the drain, and used to bore a hole through the eardrum and to insert the drain into the hole.

6 Claims, 14 Drawing Figures

DRAIN FOR THE EARDRUM AND APPARATUS FOR INTRODUCING THE SAME

This is a division, of application Ser. No. 410,688, filed Oct. 29, 1973, now U.S. Pat. No. 3,888,258.

BACKGROUND OF THE INVENTION

1. Field of the Invention

This invention relates to a drain for the eardrum and an apparatus for inserting the same into the eardrum, and more particularly to an apparatus for inserting a drain into the eardrum by which a hole is bored through the eardrum of a patient suffering from otitis media and the drain inserted into the hole in the eardrum.

2. Description of the Prior Art

As is generally known, a drain for the eardrum is inserted into a hole bored through the eardrum of an otitis media patient by a scalpel to ensure that the hole does not close and that pus generated in the middle ear will be discharged therethrough.

Conventional eardrum drains are formed of silicone rubber or polyethylene, and no method has been proposed by which the drain can be surely held in the eardrum or which will prevent the drain inserted into the hole in the eardrum from readily falling from the eardrum. Therefore, conventional drains inserted into the hole in the eardrum have often fallen from the eardrum during medical treatment for otitis media and consequently the trouble of inserting the drain into the hole in the eardrum has to be taken again.

Moreover, no special apparatus for inserting the drain into the eardrum has been developed. Consequently, when a medical man wishes to insert the drain into the eardrum of the patient, he incises the eardrum to a suitable length with a scalpel, picks up the drain with a pincette and inserts the drain into the incised eardrum. In the above-mentioned conventional method, it is very troublesome to insert the drain into the incised eardrum, and much operating time and a high level of skill are required.

If the medical man incises the eardrum too much, the drain inserted into the eardrum will be in an unstable state and there is the possibility that the inserted drain may fall from the eardrum.

SUMMARY OF THE INVENTION

An object of this invention is to provide a drain for the eardrum which does not easily fall from the eardrum when inserted.

Another object of this invention is to provide a novel apparatus for inserting a drain in the eardrum by which the drain can be easily and surely inserted.

A further object of this invention is to provide an apparatus for inserting a drain for the eardrum by which a hole is properly bored through the eardrum.

A still further object is to provide an apparatus for inserting a drain for the eardrum which includes a drain-holder holding many drains.

According to the invention, a drain for the eardrum is formed of a polymeric material having the properties of absorbency and swelling. Examples of suitable polymers include collagen, polyvinyl alcohol, and a copolymer of the methacrylate acid glycol type. Moreover, an apparatus for inserting the drain includes a needle with a sharp tip and a tube sheathing the needle. The needle projecting from the tube is inserted into the drain to hold it and then a hole is bored through the eardrum by the sharp tip. Thus, the needle is inserted together with the drain into the hole in the eardrum and only the drain is left held in the eardrum.

The above and other objects, features and advantages of this invention will become apparent from the following detailed description of illustrative embodiments shown in the accompanying drawings.

DESCRIPTION OF THE PREFERRED EMBODIMENTS

Figure 1:
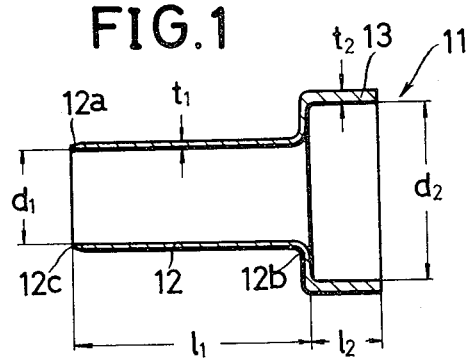
FIG. 1 is a sectional view of one embodiment of a drain for the eardrum according to the invention.

Referring to FIG. 1, one embodiment of a drain for the eardrum according to the invention will be described.

A drain 11 consists of a cylindrical main part 12 and a cylindircal ancillary part 13, formed integrally with the rear end 12b of the cylindrical main part 12 and having a larger diameter than the main part 12. The outer surface 12c of the free end 12a of the cylindircal main part 12 is tapered or rounded. The length $l_1$ of the main part 12 is preferably about 2 mm., the length $l_2$ of the ancillary part 13 about 0.6 mm., the inside diameter $d_1$ of the cylindircal main part 12 about 0.8 mm., the inside diameter $d_2$ of the cylindrical ancillary part 13 about 1.5 mm., the wall thickness $t_1$ of the main part 12 about 0.05 mm., and the wall thickness $t_2$ of the ancillary part 13 about 0.1 mm.

The drain 11 is formed of a high polymer having the properties of absorbing and swelling, for example, collagen.

Collagen is particularly preferable for the formation of the drain 11 because it dissolves over a long period, or about one week after the drain 11 has been inserted into the eardrum. The advantages arising from the properties of absorbency and swelling, and of dissolubility, will be described below. When only properties of absorbency and swelling are required, polyvinyl alcohol, a copolymer of the methacrylate acid glycol type (sold under the trade name "Hydron"), mannitol, or certain of fluorine-containing resins, or the combination of these, may be used for the formation of the drain 11. However, the above-mentioned materials have to a greater or lesser extent also the property of dissolubility.

Next, one embodiment of an apparatus 21 for inserting the drain 11 will be described with reference to FIGS. 2 to 4.

A boss 23 is formed on the upper end of a handle 22 made of metal or synthetic resin. A cylindrical metallic body 25 is attached to the handle 22 by a screw 24 at the boss 23. A metallic tube 27 is attached by a screw thread to the leading end 25a of the cylindrical metallic body 25 through a connecting element 26. A metallic needle 28 with a sharp tip 28a is movably received in the tube 27 and, in the interior 29 of the cylindircal metallic body 25, the rear end 28b of the needle is fixed to a contact element 30 which is in contact with an upper end 31a of a trigger 31 supported rotatably on an axis 32. A compression spring 33 is disposed between the connecting element 26 and the contact element 30 to return the needle 28 to its original position.

Figure 3:
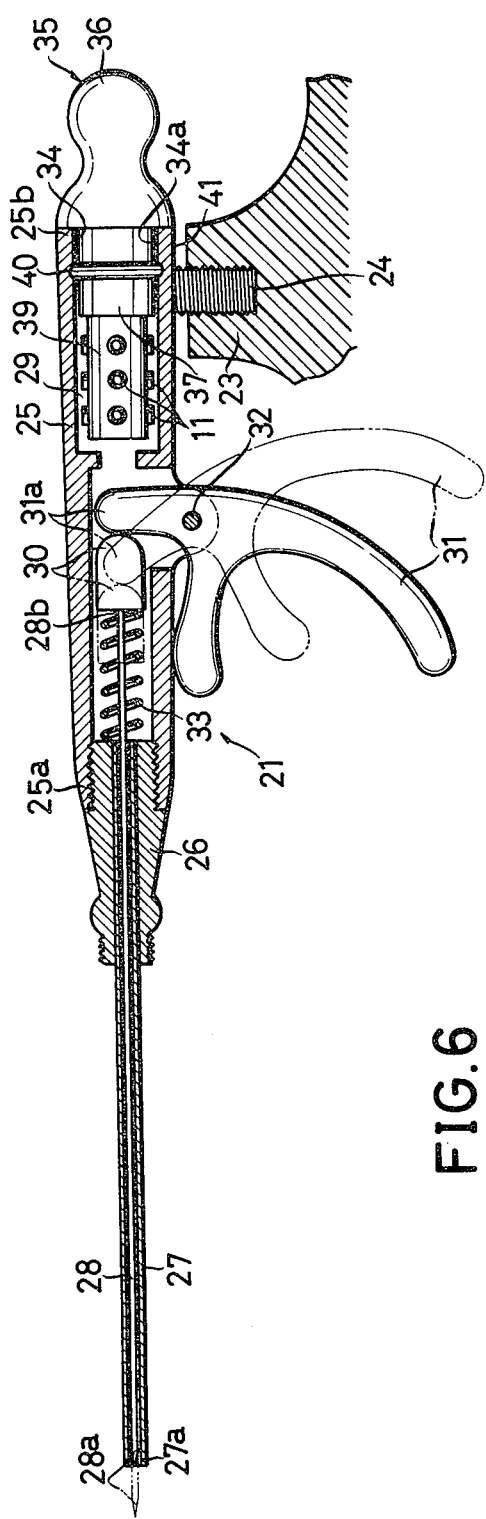
FIG. 3 is a greatly enlarged detailed vertical sectional view of an imprtant part of the embodiment shown in FIG. 2.

A suitable length of needle 28 can be extended from the tip end 27a of the tube 27 by grasping the handle 22 and drawing the trigger 31 (to rotate it anticlockwise around the axis 32 as shown in FIG. 3), so that the upper end 31a of the trigger pushes the contact element 30 and the needle 28 moves forward in the tube 27 against the compression spring 33.

When the trigger 31 is released, the trigger and the needle 28 are automatically returned to their original positions by the compression spring 33, so that the tip 28a of the needle 28 is again withdrawn within the tip end 27a of the tube 27. The outside diameter of the needle 28 is equal to or a little smaller than the inside diameter of the main part 12 of the drain 11 so that the needle 28 can be inserted into the main part of the drain. The inside diameter of the tube 27 is equal to or a little larger than the inside diameter of the main part 12 of the drain 11 so that the tip end 27a of the tube 27 can contact the bottom of the ancillary part 13 of the drain 11. The outside diameter of the tube 27 is about 1 mm.

Figure 4:
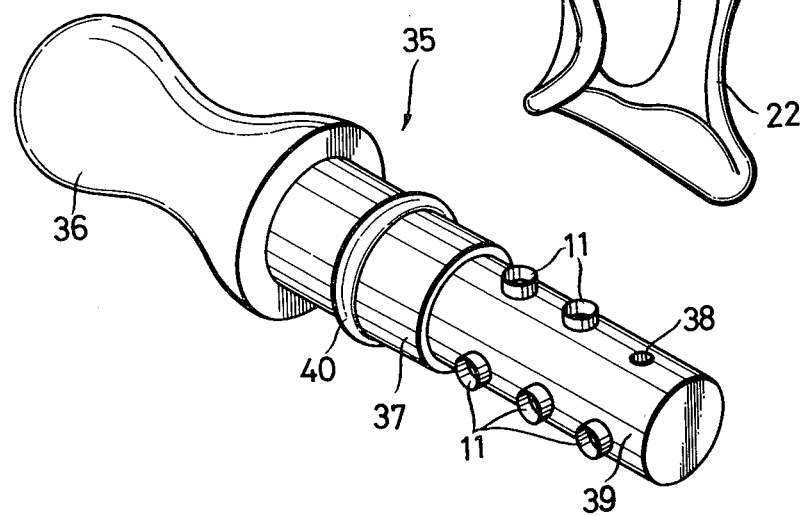
FIG. 4 is a persepective view of the drain-holder shown in FIG. 2.

An opening 34 is formed in the rear end 25b of the cylindrical metallic body 25, where a drain-holder 35 as shown in FIG. 4 is removably mounted. The drain-holder 35, made of synthetic resin, comprises a knob 36, an axially extending portion 37 for mounting, an axially extending drain-holding portion 39 having numerous holes 38 for drains 11, and an annular bulge 40 formed on the surface of the mounting portion 37. The main part 12 of each drain 11 is inserted into a respective hole 38. The drain-holder 35 is mounted at the rear end 25b of the cylindrical metallic body 25 by the elastic-fitting of the bulge 40 in an annular groove 41 formed on the cylindrical inner surface 34a of the opening 34.

Next, a method of using the drain-inserting apparatus 21 will be described.

Figure 5A:
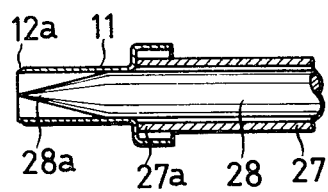
FIG. 5A to 5H are partly enlarged vertical sectional views showing one manner of inserting a drain into the eardrum according to the invention and removal of the inserted drain.
Figure 5B:
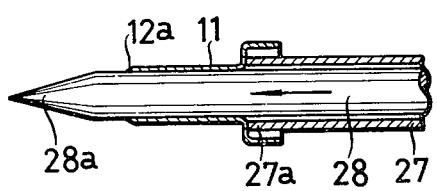

The drain-holder 35 is drawn out from the rear end 25b of the cylindrical metallic body 25, and the tip end 28a of the needle 28 is inserted into one of the drains 11 held in the drain-holder 35. For this purpose, the trigger 31 of the drain-inserting apparatus 21 is drawn by the forefinger so that the tip 28a of the needle 28 projects by about 2 mm. from the tip end 27a of the tube 27. The drain 11 is taken out from the drain-holder 35, being held by the tip 28a of the needle 28, as shown in FIG. 5A, since the diameter of the hole 38 is only a little larger than the outside diameter of the main part 12 of the drain 11 and the friction between the surface of the hole 38 and the outer surface of the main part 12 is smaller than the friction between the surface of the tip 28a of the needle 28 and the inner surface of the main part 12. After the tip 28a of the needle 28 has been inserted into the drain 11, the trigger 31 of the drain-inserting apparatus 21 is further drawn to extend the tip 28a by a further 2mm. from the tip end 27a of the tube 27, as shown in FIG. 5B.

Figure 5C:
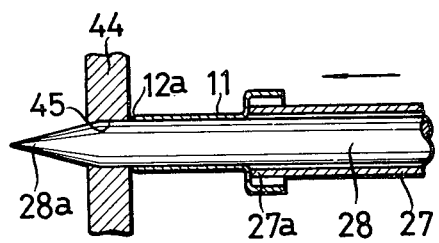
Figure 5D:
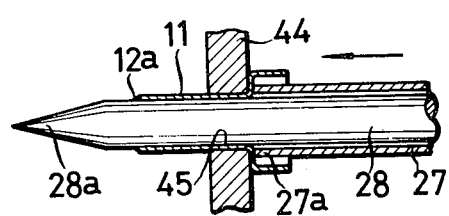
Figure 5E:
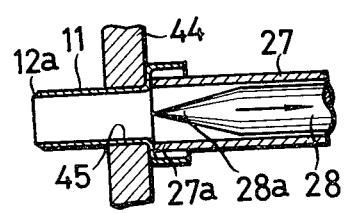
Figure 5F:
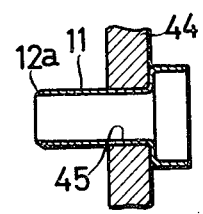

Next, a hole 45 for drain-insertion is bored through the eardrum 44 by the sharp tip 28a of the needle 28 projecting from the end 12a of the drain 11, as shown in FIG. 5C. Furthermore, the tip 28a and the drain 11 are inserted into the hole 45 by pressing on the bottom of the ancillary part 13 of the drain 11 with the tip end 27a of the tube 27, as shown in FIg. 5D. As shown in FIG. 5E, the tip 28a of the needle 28 is then withdrawn into the tube 27 by releasing the trigger 31 of the apparatus 21 while the bottom of the ancillary part 13 of the drain 11 is still being pressed by the tip end 27a of the tube 27, as shown in FIG. 5D. Thus, only the drain 11 is left inserted in the hole 45, as shown in FIG. 5F.

Figure 5G:
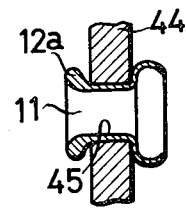
Figure 5H:
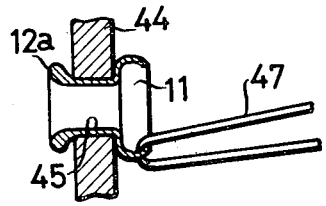

Pus formed in the middle ear is drained out to the outside of the eardrum or into the outer ear, through the drain 11 inserted into the eardrum, as above-described. Because the drain 11 is made of high polymer with the property of absorbing and swelling, it absorbs water to swell in a short time after insertion into the eardrum, as shown in FIG. 5G. It is mainly the end portion 12a of the main part 12 of the drain 11 that swells. The swelling-rate of the drain 11 is preferably over 10%, and more preferably over 20%, for example 20–30%. By such absorption and swelling, the drain 11 is prevented from readily falling from the eardrum 44, the eardrum 44 being located between the swollen end 12a of the main part 12 of the drain 11 and the ancillary part 13 of the drain, so that the drain 11 unexpectedly does not fall from the eardrum 44 during medical treatment, but is securely held in the eardrum 44 till the otitis media is perfectly healed. After perfect healing of the otitis media, or as occasion demands, the drain 11 can be easily taken out from the eardrum 44 by gripping the ancillary part 13 of the drain 11 with a pincette 47 or the like, as shown in FIG. 5H.

When the drain 11 is formed of collagen, it is not necessary to take the drain 11 out from the eardrum 44, but rather the drain 11 may be left inserted into the eardrum 44, because it naturally dissolves and at length disappears. In other words, when the drain 11 is formed of a high polymer having the property of dissolving over a long period, it is not necessary to take out the drain 11 from the eardrum 44 after healing of the otitis media.

Figure 2:
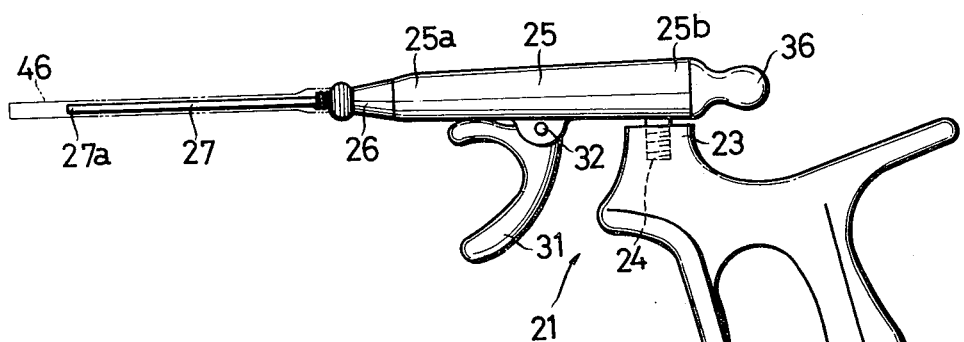
FIG. 2 is a side view of one embodiment of a drain-inserting important according to the invention.

When the drain-inserting apparatus 21 is not in use, the drain-holder 35 is fitted into the opening 34 and the tube 27 is covered with a guard tube 46 as shown by the chain dotted line in FIG. 2 so that the tube 27 and the needle 28 are prevented from being accidentally bent. The end of the guard tube 46 is screw threaded to the end of the connecting element 26.

Figure 7:
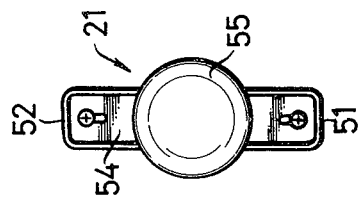
FIG. 7 is a front view of another embodiment shown in FIG. 6.
Figure 6:
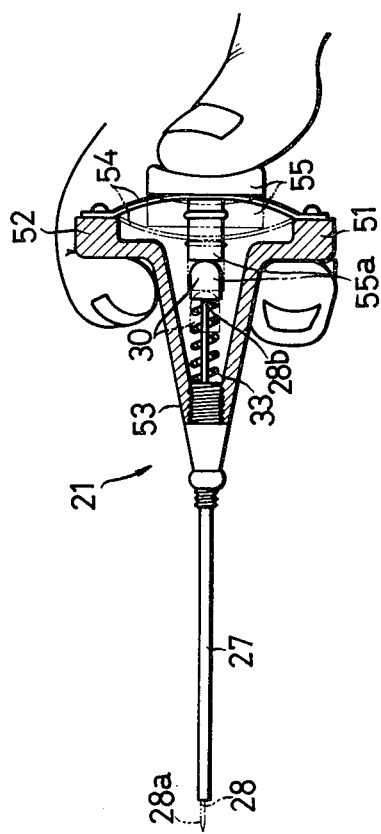
FIG. 6 is a partly sectional side view of another embodiment of drain-inserting apparatus according to the invention.

FIG. 6 and FIG. 7 show another embodiment of a drain-inserting apparatus 21 according to the invention. The parts of this embodiment corresponding to the parts of the embodiment shown in FIG. 2 and FIG. 3, carry the same reference numerals.

In this embodiment, a tube 27 is screw threaded to a drain-inserting apparatus body 53 having a pair of shoulders 51, 52 through a connecting element 26. A push button 55 is supported by a leaf spring 54 at the rear end of the body 53. One end 55a of the push button 55 is in contact with a contact element 30 fixed to the rear end 28b of a needle 28. In the operation, as in an injection syringe, the body 53 is held in such a manner that the forefinger and the middle finger are put on the pair of shoulders 51, 52 and the thumb is put on the push button 55, as shown in FIG. 6. When the push button 55 is pushed by the thumb against the leaf spring 54 it causes the needle 28 to move forward in the tube 27 against the compression spring 33, as in the first embodiment of the drain-inserting apparatus. Thus the tip 28a of the needle 28 is extended from the tip end 27a of the tube 27, and when the push button 55 is released by the thumb, the needle 28 is moved back to the original position by the compression spring 33.

By the use of the invention as above-described, the drain is prevented from falling unexpectedly from the eardrum during medical treatment and the pus formed in the middle ear is reliably discharged through the drain. Since the properties of absorbing and swelling are realized only after the drain has been inserted into the eardrum, the formed drain as it is, can be handled before being deformed by the absorption and swelling. Moreover, the drain can be very easily and rapidly inserted into the eardrum in comparison with the conventional method, in which the eardrum is incised with a scalpel and the drain is picked up with a pincette. Since with the invention the hole is bored through the eardrum by the sharp end of the needle, there is no possibility that the eardrum may be erroneously incised too much, as it may be by the scalpel in the conventional method, and the hole can be correctly bored through the eardrum.

While there have been described preferred embodiments of the invention, obviously modifications and variations are possible in light of the above teachings. It is therefore to be understood that within the scope of the appended claims, the invention may be practised otherwise than as specifically described.

What is claimed is:

1. A drain for the eardrum comprising a drain element shaped and dimensioned for insertion through a correspondingly dimensioned hole bored in the eardrum to serve as a fluid drain therethrough; said element being formed of a polymeric material capable of absorbing a portion of said fluid and thereby swelling after insertion in the eardrum, the swelling of the element securely holding the element in place during use of the drain.

2. A drain according to claim 1 wherein said drain element comprises a hollow cylindrical main drain portion and a hollow cylindrical ancillary drain portion, said ancilliary drain portion having a larger internal diameter than said main drain portion and being formed integrally therewith and extending axially therefrom at the one end thereof which is positioned on the exterior side of the eardrum.

3. A drain according to claim 2 wherein the other end of said main drain portion remote from said one end is provided with a tapered outer surface.

4. A drain according to claim 1 wherein said drain element is formed of at least one polymeric material selected from the group consisting of collagen, polyvinyl alcohol, a copolymer of the methacrylic acid glycol type, mannitol, a fluorine-containing resin having the properties of absorbency and swelling, and a combination of such polymers.

5. A drain for the eardrum according to claim 1 wherein the drain consists of the material gradually dissolvable in the eardrum.

6. A method of inserting a drain in the eardrum comprising the steps of:
    providing a hollow drain element of polymeric material having properties of absorbency and swelling and comprising a main portion and an enlarged ancillary portion at one end thereof;
    extending a needle from a protective tube therefor and inserting it through said drain element in the direction from said ancillary portion to said main portion;
    passing said needle through said eardrum;
    pressing on said tube to push said element along said needle until said main portion but not said ancillary portion has passed through said eardrum;
    withdrawing said needle into said tube;
    and removing said tube and needle from said drain leaving said drain in position.

* * * * *